United States Patent [19]

Saraf

[11] 4,425,787

[45] Jan. 17, 1984

[54] METHOD OF AND APPARATUS FOR MEASURING THE DENSITY PROFILE OF A LIQUID LAYER

[75] Inventor: Israel E. Saraf, Jerusalem, Israel

[73] Assignee: Solmat Systems Ltd., Yavne, Israel

[21] Appl. No.: 302,576

[22] Filed: Sep. 15, 1981

[51] Int. Cl.³ .......................... G01N 9/00; G01N 9/26
[52] U.S. Cl. ...................................... 73/32 R; 73/438
[58] Field of Search ................................ 73/32 R, 438

[56] References Cited

U.S. PATENT DOCUMENTS 3,287,979  11/1966  Dohring ................................ 73/483
3,392,588   7/1968  Hillman ................................. 73/438
4,249,518   2/1981  Holt .

FOREIGN PATENT DOCUMENTS 1177 of 1862 United Kingdom ............... 73/32 R

Primary Examiner—James J. Gill
Attorney, Agent, or Firm—Sandler & Greenblum

[57] ABSTRACT

Apparatus for measuring the density profile of a layer of liquid includes a plurality of individual tubes arranged in side-by-side fashion, each of the tubes having an inlet opening in its lower end. A vacuum manifold is connected to the apertured upper ends of the tubes. The apertures in the lower ends of the tubes are vertically staggered and the tubes are vertically oriented with the lower ends of the tubes immersed in the liquid, so that the inlet openings are differentially spaced from the surface of the liquid. The application of a vacuum to the tubes causes liquid from the different levels to be drawn into the tubes, the height of the liquid in the tubes above the surface being proportional to the density of the liquid drawn into the tubes through the inlets.

10 Claims, 6 Drawing Figures

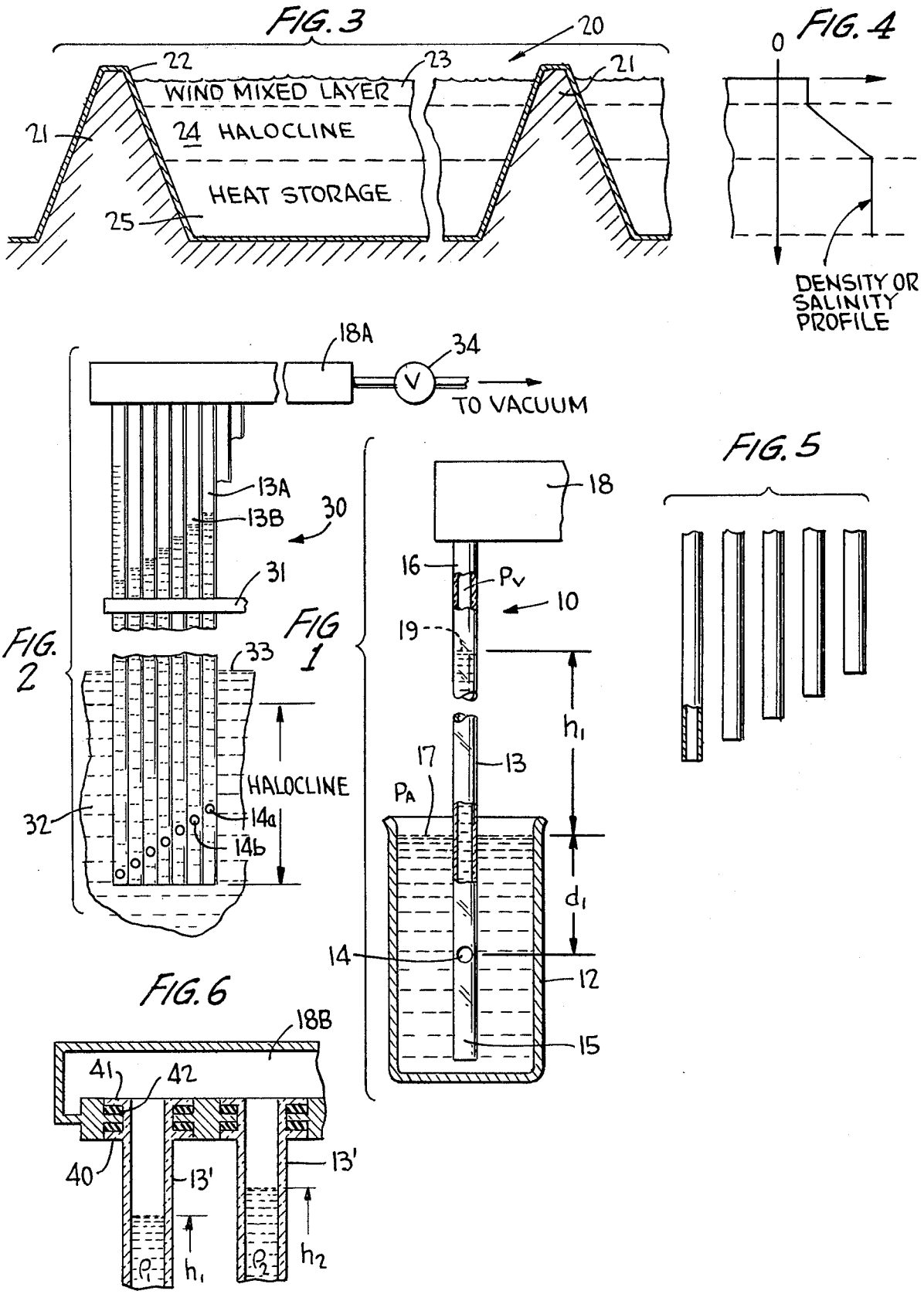

METHOD OF AND APPARATUS FOR MEASURING THE DENSITY PROFILE OF A LIQUID LAYER

DESCRIPTION

1. Technical Field

This invention relates to a method of and apparatus for measuring the density profile in a liquid layer, and is particularly suitable for measuring the density profile of a halocline in a salt solar pond.

2. Background Art

A salt solar pond is a body of water having a nonconvective layer, called a halocline, located just below the surface of the water. The halocline, which is usually about 1–1.5 m deep, has a downwardly directed density gradient achieved by a salinity that changes from about 5% near the top of the halocline to around 30% near the bottom. Covering the halocline is a wind-mixed layer from 10–50 cm deep, depending on weather conditions, this layer having a uniform salinity of around 5%. Below the halocline is water of uniform salinity, about 30%, which forms the heat storage layer of the pond.

Solar radiation incident on the surface of the pond penetrates into the halocline and into the heat storage layer, and is absorbed, thereby heating the water. Heated water in the wind-mixed layer below the surface is lighter than the cooler surface water; and the differences in densities throughout the wind-mixed layer establish convection currents that rapidly transfer the warmer water in the wind-mixed layer to the surface, where the absorbed heat is dissipated to the atmosphere. The temperature of the wind-mixed layer thus approximates ambient temperature.

Water in the halocline heated by the absorption of solar radiation also becomes lighter; but the density profile of the halocline, which closely matches the salinity profile, ensures that the density of a lower heated stratum exceeds the density of the stratum immediately thereabove, with the result that convection currents in the halocline are suppressed. Consequently, after a period of time a temperature profile is established in the halocline which, in general, matches the salinity profile. Ultimately, the water in the heat storage layer is heated; and the heated water in this layer is protected against conductive heat loss to the atmosphere by the halocline, which thus acts as an insulator. In this manner, the temperature of the water in the heat storage layer can reach 90°–100° C.

In southern California and comparable latitudes, the heat transferred by conduction to the heat storage layer averages about 40–50 watts/m$^2$ (on a 24-hour, yearly basis), so that a 60-acre pond is adequate to provide heat for a power plant capable of producing 5 MW peak power for about 4 hours per day. If the heat storage layer were to reach a temperature of 80° C., the depth of the heat storage layer would be about 2–3 m.

Any action that significantly disturbs the density profile of the halocline, as, for example, uncontrolled mixing that deepens the wind-mixed layer, would expose the heated brine to the atmosphere, destroying the ability of the pond to store heat. Repairs to the density profile of the halocline can be carried out by preparing a brine of appropriate density, then selectively injecting a predetermined amount of the brine into the pond at the depth at which repair is to be made, the density of such brine being predetermined in accordance with the degree of damage to the profile.

It has been found from experience that changes in the profile of the halocline occur rather slowly, except in cases of violent storms. However, when the solar pond is associated with a power plant, wherein reliability is essential, monitoring of the profile of the halocline is critical in order to detect any perturbation, and to remedy it as soon as possible.

Conventionally, monitoring of the profile of the halocline is achieved by pumping samples from the halocline at different depths, and then making measurements with a hydrometer to determine the specific gravity of each sample of water. Because of the time involved in carrying out the hydrometer measurements, some cooling of the liquid samples is bound to occur; and this cooling will introduce errors in the density measurements. Thus, the conventional technique for determining the density profile of a halocline is time-consuming, and subject to many inaccuracies.

It is, therefore, an object of the present invention to provide a new and improved method of and means for measuring the density profile of a liquid layer which is faster and more convenient than the techniques previously utilized.

DISCLOSURE OF INVENTION

Apparatus in accordance with the present invention measures the density of a liquid by using axial tube means having a lower apertured end for insertion into the liquid, and an apertured upper end for extending above the surface of the liquid. When a vacuum is applied to the apertures in the upper end of the tube means, liquid is drawn into the tube means to a height above the surface of the liquid proportional to the density of the liquid that enters the lower apertured end of the tube means when the vacuum is applied.

The liquid in the tube means can be considered as comprising two components: a slug whose length is the submergence of the lower apertured end of the tube means, and whose density is the average density of the liquid between the surface of the liquid and the lower apertured end, and a slug whose length is the height of the liquid in the column above the surface of the liquid, and whose density is the density of the liquid at the depth of the aperture in the lower end of the tube means. Under static conditions, the pressure in the liquid surrounding the lower apertured end of a tube is equal to the pressure inside the tube. Analytically, $$P_{outside} = P_{inside} \tag{1}$$

$$P_a + \rho_{avg} g d_1 = P_v + \rho_{avg} g d_1 + \rho_1 g h_1 \tag{2}$$

where the quantity $P_a$ is the pressure at the surface of the liquid, $\rho_{avg}$ is the average density of the liquid between the surface of the liquid and the depth of the inlet opening in the tube means, g is the gravitational constant, $d_1$ is the submergence of the inlet end of the tube means, $P_v$ is the pressure inside the tube (vacuum), $\rho_1$ is the density of liquid at the depth $d_1$ of the inlet opening, and $h_1$ is the height of the liquid in the tube means above the surface of the liquid. Simplifying and rearranging shows the following:

$$\Delta P = P_a - P_v = \rho_1 g h_1 \tag{3}$$

Inspection of eq. (3) shows that given the difference in pressure between the vacuum inside the tube and the pressure outside the tube, and given the constant g, the density of liquid at the depth $d_1$ is inversely proportional to $h_1$, which is the height of the liquid in the column above the surface of the liquid.

Preferably, the apparatus is constructed such that the tube means comprises a plurality of individual tubes arranged in side-by-side fashion, each having an inlet opening in its lower end and a vacuum manifold connected to the apertured upper ends of the tubes. When the apertures in the lower ends of the tubes are staggered and the tube means is vertically oriented with the lower ends of the tubes immersed in liquid, the inlet openings are differently spaced from the surface of the liquid. This arrangement is particularly suited for determining the density profile of a layer of liquid, e.g., the halocline of a solar pond. In such case, the tubes are connected via their inlet openings to respective strata of the halocline; and, when a vacuum is applied to the vacuum manifold, the height to which the liquid in each tube rises above the surface of the liquid is proportional to the density of the liquid in the stratum connecting to the inlet opening in the tube. Consequently, the distribution in height of the liquid in the various tubes is a measure of the density profile of the liquid in the layer with which the inlet openings of the tubes are connected. By making the tubes transparent, visual inspection, as well as measurement of the heights of the liquids, can be carried out for the purpose of recording the density profile at a given instant in time.

BRIEF DESCRIPTION OF THE DRAWINGS

An embodiment of the present invention is disclosed in the accompanying drawings, wherein:

FIG. 1 is an elevation, with parts partially cut away, of apparatus according to the present invention utilizing a single tube for measuring the density of a liquid at a predetermined depth;

FIG. 2 is a second embodiment of the present invention, showing a plurality of tubes for simultaneously obtaining a measure of the density at a plurality of depths in a liquid;

FIG. 3 is a schematic sectional view of a salt solar pond with which the apparatus of the present invention can be used;

FIG. 4 is a plot showing the density profile within the pond of FIG. 3;

FIG. 5 is a variation of the submerged ends of the tubes for obtaining samples of liquid at different depths; and FIG. 6 is a sectional view of a constructional detail of the apparatus shown in FIG. 2.

DETAILED DESCRIPTION

Referring now to FIG. 1 of the drawing, reference numeral 10 designates apparatus according to the present invention for measuring the density of liquid 11 at a depth $d_1$ contained in vessel 12. Apparatus 10 comprises axial tube 13 having inlet aperture 14 in its lower end 15, and an apertured upper end 16 that extends above surface 17 of the liquid. Vacuum manifold 18 connected to the upper end 16 of tube 13 applies a negative pressure to the inside of tube 13, the negative pressure being the value $P_v$, which is below atmospheric pressure $P_a$, to which surface 17 of the liquid is exposed. By reason of the vacuum in tube 13, liquid from depth $d_1$ in liquid 11 is drawn through inlet opening 14 and into tube 13, where the liquid level rises to the height $h_1$, as shown in the drawing. If the volume of liquid drawn into opening 14 when the vacuum becomes effective is small in comparison to the volume of liquid in vessel 12, then level 17 will not change significantly. In such case, the density of liquid at the depth $d_1$ is inversely proportional to the height of the column of liquid in tube 13, namely, the value $h_1$.

The height $h_1$ of the column of liquid 19 in tube 13, and the density of the liquid at the depth $d_1$, can be understood by considering the effect on column 19 by reason of the vacuum. First, consider that the pressure inside tube 13 is atmospheric pressure, i.e., the pressure inside the tube is the same as the pressure on surface 17. If the tube were carefully placed in vessel 12 so as not to disturb any density gradients within the vessel, liquid would enter the tube through inlet 14 as the tube were lowered to a depth $d_1$. In such case, the level of liquid in the tube would rise, and match the level of the liquid outside the tube; and the slug of liquid in the tube would match the liquid outside the tube. If it were possible to mix the liquid slug in the tube without disturbing the liquid outside the tube, the density of the liquid inside the tube would be the mean of the density measured between surface 17 and the depth $d_1$ of inlet opening 14. Furthermore, the pressure inside the tube due to the static head of the slug of liquid therein is exactly equal to the static pressure at the inlet outside the tube due to the remainder of the liquid in vessel 12.

When a vacuum is applied inside tube 13, the liquid therein rises, causing liquid at the level of inlet 14 to flow into the tube as the liquid level in the tube rises. By slowly applying the vacuum, liquid will be drawn into the tube essentially from a stratum at depth $d_1$.

When equilibrium is once more established, which means that the pressure in the tube at inlet 14 is equal to the pressure outside the tube at inlet 14, the situation given by eq. (2) will obtain. That is to say, sufficient liquid from the stratum at depth $d_1$ will be drawn into the tube to establish a slug of liquid extending above surface 17, which will balance the difference in pressure inside and outside the tube. Eq. (3) expresses the relationship between the difference in pressure across the tube, the density of the liquid, and the height of the liquid above the surface.

By increasing the vacuum on the tube (i.e., by increasing the pressure differential across the tube), the height of the liquid in the tube can be raised. If the level can be read to an accuracy of 1 mm, and the height of the column of liquid above the surface is 200 cm, the error in reading will be 1 part in 2000, or 0.05%.

Apparatus 10 can be used for the purpose of monitoring the halocline of salt solar pond 20, which is illustrated in FIG. 3. Pond 20 comprises side embankments 21, which may be earthen and covered with an impervious liner 22 for sealing the earthen embankments and the bottom of the pond against leakage of the water in the pond. As shown in FIG. 3, pond 20 comprises an upper, wind-mixed layer 23 of uniform salinity (0-5%) covering halocline 24, having a downwardly directed density gradient, which overlies heat storage layer 25 of uniform salinity. FIG. 4 shows the density profile through the pond, such profile closely matching the salinity profile. In a conventional pond, the salinity in the halocline increases from around 5% to around 30%, while the heat storage layer is of uniform salinity, around 30%.

Solar radiation penetrates into the solar pond, and is absorbed in the wind-mixed layer, as well as in the halocline and the heat storage layer. Because of the turbulent nature of the wind-mixed layer, water warmed by absorption of solar radiation quickly rises to the interface, and is dissipated to the atmosphere. Thus, the temperature of the wind-mixed layer is substantially uniform, and approximates ambient temperature.

Because of the sharp downwardly increasing density gradient in the halocline, the absorption of heat by a stratum in the halocline does not reduce its density below the density of the stratum immediately above, with the result that the halocline is stratified, and is non-convective. In other words, heat is absorbed within the halocline, and the temperature profile in the halocline closely matches the salinity profile shown in FIG. 4. Eventually, heat is transferred into the heat storage layer, which becomes quite hot and, in many cases, approaches 100° C.

It is conventional to utilize the heat storage layer of a solar pond as the heat source for a power plant. In such case, it is essential to maintain the salinity profile in the halocline, which serves as an insulator for protecting the heat storage layer against heat loss due to convection to the atmosphere. Various expedients are known for maintaining the halocline against molecular diffusion of salt, and for correcting the halocline in the event of storms that increase wind-mixing at the surface. One technique that is available is disclosed in U.S. Patent Application Ser. No. 149,564, filed May 14, 1980, which involves selectively mixing water from the halocline taken at different levels and discharging the mixed water into an intermediate level.

In order to determine the status of the halocline, it is essential to continuously monitor the density profile. The present invention is ideally suited for this task in the embodiment illustrated in FIG. 2. Apparatus 30, shown in FIG. 2, comprises a plurality of individual tubes 13A, 13B, etc., the tubes being clamped together at 31 in a side-by-side lateral arrangement. Each of the tubes of apparatus 30 is provided with an inlet opening in its lower end. Specifically, tube 13A is provided with inlet opening 14A, etc. When the tube means defined by the bundle of tubes is vertically oriented, with the lower ends of the tubes immerged in liquid 32, the inlet openings 14A, 14B, etc. are differently spaced from surface 33 of the liquid. As shown in FIG. 2, apparatus 30 is deployed so that the inlet openings are located at different strata in halocline 32.

The upper end of each of the tubes terminates in vacuum manifold 18A, which is connected by three-way valve 34 to a vacuum pump (not shown). Valve 34 is selectively operable to close vacuum manifold 18, to vent it to the atmosphere, and to connect it to a vacuum pump.

In operation, valve 34 is actuated so that manifold 18A is opened to atmospheric pressure, and apparatus 30 is slowly inserted into the solar pond until the staggered inlet apertures are located within halocline 32. As indicated previously, liquid enters the tubes through the inlet openings, and eventually, the liquid level inside each of the tubes will rise to the level of surface 33. When this has been accomplished, valve 34 is closed to the atmosphere, and opened momentarily to the vacuum pump before being closed to maintain the vacuum, which causes the liquid in the tubes to rise to different levels, as indicated in FIG. 2, depending on the density of the liquid entering the tubes in response to the vacuum. The height of the liquid in each tube is thus a measure of the density in the halocline at a depth corresponding to the depth of the inlet to the tube. Because the tubes are transparent, the different heights of the liquid in each of the tubes can be determined by visual inspection, or can be photographed for reference purposes. To facilitate a reading of the heights, the tubes may be provided with graduations (not shown).

In order to provide a reference level to compare the levels obtained using water from the halocline, a calibration process may be carried out. In such case, one or more of the tubes of apparatus 30 may be placed in a container of distilled water, for example, and a predetermined vacuum applied to manifold 18. The level of water in the container is adjusted to take into account the depth of the inlet to the tube in its normal mode of operation by adding or removing water from the container. When the depth of the opening in the tube below the level of the surface of the water is the same as in actual use in a halocline, the height of the column of water in the tube will represent a reference for a density of unity. This can be utilized to obtain the specific gravity of the various levels of the halocline by directly reading the graduations on the tubes.

Instead of calibrating the system in this manner, one of the tubes of the apparatus can be associated with a container of distilled water, which would then be lowered into the halocline with all the tubes. In this case, however, the container is long enough that water from the pond does not mix with the water in the container. In this instance, the vacuum pulled by the manifold need not be ascertained accurately, and the level to which the distilled water in the calibration tube rises will constitute a reference against which the levels in the other tubes can be compared.

In the embodiment shown in FIG. 2, the inlet openings are provided as holes in the sides of the various tubes. In the embodiment shown in FIG. 5, however, the openings are provided on the free ends of the tubes. That is to say, the tubes are terminated in staggered fashion so that the openings thereof will be at different depths when the apparatus is inserted into the halocline.

FIG. 6 shows an arrangement for connecting the tubes to vacuum manifold 18B. Specifically, tubes 13' pass through apertures in the lower end of the manifold, and the end of the tube is captured between nuts 40, 41 and washers 42.

Readings obtained from the apparatus shown in FIG. 2 can be obtained manually, as described above, by visually observing the level of liquid in the tubes. The relative heights can be recorded, and then plotted against the vertical positions of the inlets. Alternatively, or in addition, a camera may record the heights periodically on an automated basis, as required. Because the liquid in each of the tubes will be of a different temperature when the apparatus is used for monitoring the profile of the halocline, very accurate readings will require making a correction that takes into account the differences in density due to the differences in temperature. The correction factor that must be applied varies from zero near the top of the layer, which is in thermal equilibrium with the environment, to a maximum at the lowest level, which, of course, is the warmest. The value of the correction can be found experimentally by calibration, or can be obtained by a theoretical analysis by multiplying the average value of thermal expansion of the liquid.

In one example of the apparatus, sixty tubes are utilized, each tube being 0.4 cm in diameter, providing apparatus that has a 40 cm width. The total length is approximately 380 cm, which allows the inlets to the tubes to extend a distance of approximately 150 cm from the lower end of the tubes. The height of the tubes between the last inlet opening and the vacuum manifold is approximately 230 cm, which permits a 200 cm elevation for liquid from the least dense region of the halocline.

In order to ensure that the readings are accurate, it is essential to eliminate any liquid in the tubes before the apparatus is inserted into the pond. In order to ensure this, a wash with an anti-wetting agent is performed. From actual experience, it has been found that the total error of the various types referred to above, namely, the reading error and errors due to failure to completely dry the insides of the tubes is of the order of magnitude of $\pm 1.5 \times 10^{-3}$ g/cm$^3$. This error, of course, can be reduced by carefully inserting the apparatus into the liquid, and by using longer tubes.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

What is claimed is:

1. Apparatus for measuring the density of a liquid comprising a plurality of individual tubes arranged side-by-side, each tube having an inlet aperture in its lower end, and a vacuum manifold connected to the apertured upper ends of the tubes, the lower ends of the tubes being staggered so that, when the tubes are vertically oriented with the lower ends thereof immersed in the liquid, the inlet openings are differently spaced from the surface of the liquid, whereby liquid from different levels is drawn into the tubes when a vacuum is applied to the vacuum manifold.

2. Apparatus according to claim 1 wherein the inlet apertures of the tubes are located at the bottom free ends of the tubes.

3. Apparatus according to claim 1 wherein the inlet apertures of the tubes are located in the sides of the tubes.

4. Apparatus according to claim 3 wherein the tubes are transparent, and are marked with graduations adjacent the upper ends for effecting the measurement of the height of liquid in the tubes.

5. Apparatus according to claim 3 wherein the tubes are polycarbonate.

6. A combination of apparatus according to claim 3 with a salt solar pond having an upper wind-mixed layer of uniform salinity covering an intermediate halocline with a downwardly directed density gradient, and a lower heat storage layer of uniform salinity covered by the halocline, wherein the inlet apertures of the tubes lie within the halocline.

7. A method for measuring the density profile of a solar pond having a halocline with a downwardly directed density gradient comprising simultaneously establishing a plurality of columns of liquid respectively associated with different levels of the halocline, each column including liquid from the level with which the column is associated, such that the height of a column above the surface of the liquid is proportional to the density of the liquid at the depth associated with the column.

8. A method according to claim 7 wherein the column of liquid contains liquid whose density is the average density of the liquid between the surface and the predetermined depth.

9. A method according to claim 8 including measuring the differences in height between the various columns to determine the relative density profile in the layers.

10. A method according to claim 8 wherein each column of liquid is established in a tube whose lower end is submerged below the liquid, and which has an opening at a depth corresponding to the stratum of interest in the layer, the method including establishing a vacuum on the upper end of the tube for raising a column of liquid in the tube to a height proportional to the density of liquid at a depth defined by the opening in the tube.

* * * * *